United States Patent
Davis (10) Patent No.: US 9,717,603 B2
(45) Date of Patent: Aug. 1, 2017

(54) IMPLANTABLE FACET FUSION DEVICES

(71) Applicant: Timothy T. Davis, Santa Monica, CA (US)

(72) Inventor: Timothy T. Davis, Santa Monica, CA (US)

(*) Notice: Subject to any disclaimer, the term of this patent is extended or adjusted under 35 U.S.C. 154(b) by 54 days.

(21) Appl. No.: 13/770,713

(22) Filed: Feb. 19, 2013

(65) Prior Publication Data

US 2013/0253649 A1    Sep. 26, 2013

Related U.S. Application Data

(60) Provisional application No. 61/600,185, filed on Feb. 17, 2012.

(51) Int. Cl.
| | | |
|---|---|---|
| *A61F 2/44* | (2006.01) | |
| *A61F 2/46* | (2006.01) | |
| *A61B 17/16* | (2006.01) | |
| *A61B 17/70* | (2006.01) | |
| *A61B 17/00* | (2006.01) | |

(52) U.S. Cl.
CPC .......... *A61F 2/446* (2013.01); *A61B 17/1615* (2013.01); *A61B 17/1671* (2013.01); *A61B 17/7064* (2013.01); *A61F 2/46* (2013.01); *A61B 2017/00004* (2013.01)

(58) Field of Classification Search
CPC ..... A61B 17/84; A61B 17/844; A61B 17/864; A61B 17/8625; A61B 2017/8655
USPC .... 606/246–249, 300–321; 623/17.11–17.16
See application file for complete search history.

(56) References Cited

U.S. PATENT DOCUMENTS

| | | | |
|---|---|---|---|
| 4,878,915 A | 11/1989 | Brantigan | |
| 6,582,467 B1 | 6/2003 | Teitelbaum et al. | |
| 6,660,008 B1* | 12/2003 | Foerster | A61B 17/0401 |
| | | | 411/34 |
| D574,957 S | 8/2008 | Petersen | |
| D581,538 S | 11/2008 | Horton | |
| 7,691,148 B2 | 4/2010 | Michelson | |
| 8,343,189 B2* | 1/2013 | Assell | A61F 2/4405 |
| | | | 606/246 |
| 2004/0010312 A1 | 1/2004 | Enayati | |
| 2005/0049590 A1 | 3/2005 | Alleyne et al. | |
| 2005/0143825 A1 | 6/2005 | Enayati | |
| 2005/0187555 A1* | 8/2005 | Biedermann | A61B 17/68 |
| | | | 606/62 |
| 2005/0222681 A1 | 10/2005 | Richley et al. | |
| 2005/0261771 A1 | 11/2005 | Paul et al. | |
| 2007/0038219 A1* | 2/2007 | Matthis | A61B 17/864 |
| | | | 623/17.11 |
| 2008/0015695 A1 | 1/2008 | Eckman | |
| 2009/0030461 A1 | 1/2009 | Hoy et al. | |
| 2009/0036927 A1 | 2/2009 | Vestgaarden | |
| 2009/0171461 A1 | 7/2009 | Conner et al. | |

(Continued)

*Primary Examiner* — Ellen C Hammond
*Assistant Examiner* — Christina Negrellirodrigue
(74) *Attorney, Agent, or Firm* — MH2 Technology Law Group, LLP (57) ABSTRACT

Implantable devices for the treatment of degenerative facet joint disease, and more specifically to implantable devices for the immobilization or fusion of degenerated facet joints, particularly of the cervical spine are provided. The devices may be easily inserted into the facet joint, promoting fusion and initiating a natural healing response. Also provided are methods of treating degeneration of a facet joint using these implantable devices.

19 Claims, 11 Drawing Sheets

(56) References Cited

U.S. PATENT DOCUMENTS

2010/0121378 A1    5/2010   Malek
2010/0191241 A1    7/2010   McCormack et al.

\* cited by examiner

IMPLANTABLE FACET FUSION DEVICES

CROSS-REFERENCE TO RELATED APPLICATIONS

This application claims priority to U.S. Provisional No. 61/600,185 filed Feb. 17, 2012 and entitled "Implantable Facet Fusion Devices," the content of which is incorporated by reference in its entirety.

FIELD

The present disclosure relates to implantable devices for the treatment of degenerative facet joint disease, and more specifically to implantable devices for the immobilization or fusion of degenerated facet joints, particularly of the cervical spine.

BACKGROUND

Facet joints are the hinge-like joints that connect vertebrae together. They are located at the back of the spine (posterior), and work alongside the vertebral discs to form a functional working unit of the spine. These joints help support the weight of the vertebra, and control movement between individual vertebrae of the spine, such as flexion, extension and twisting motions. In addition, the facet joints are synovial joints, which means each joint is surrounded by a capsule of connective tissue and produces a fluid to nourish and lubricate the joint. Cartilage coats the joint surfaces and allows the joints to move or glide smoothly against each other.

As with other bone joints, facet joints are almost constantly in motion with the spine, and are therefore susceptible to degeneration such as from osteoarthritis. Degenerative facet joint disease is a type of osteoarthritis that can cause the break down of the cartilage covering the facet joint surfaces, the result of which is joint inflammation-degradation in the spine that can lead to bone spurs or enlargement of the joints. The disease itself may be due to simple wear and tear associated with aging, or due to severe obesity. The predominant symptom is back pain on motion, particularly at the joint or joints where the condition is present. Other symptoms that can occur are swelling, reduced range of motion, and muscle weakness.

There is no known cure for spinal osteoarthritis. Current treatments focus on reducing pain and slowing down the disease progression. These treatments vary depending on the degree of joint damage but can include lifestyle changes, over-the-counter or prescription painkillers and physical therapy. Another common treatment is injection into the affected facets, such as with an anesthetic numbing agent for shorter-term results or a corticosteroid for longer-term results.

Like other bone joints that have degenerated, more invasive treatments such as surgery may be used in certain cases. It can be useful to immobilize the affected spinal motion segment in order to stabilize the spine as well as reduce the pain associated with motion of the damaged joint. This can be particularly applicable in the cervical spine, where chronic neck pain is prevalent in interventional pain management practices. Accordingly, it is desirable to provide implantable devices that are well suited for immobilization of diseased facet joints, and in particular cervical facet joints. The implantable devices should be easy to implant and provide structural integrity to the area to be treated. Even more desirable are implantable devices that also promote fusion of the damaged cervical facet joint in order to provide a longer-term solution to chronic neck pain.

SUMMARY

The present disclosure provides implantable devices for the treatment of degenerative facet joint disease, and more specifically to implantable devices for the immobilization or fusion of degenerated facet joints, particularly of the cervical spine.

In one embodiment, an implantable device for cervical facet fusion is provided. The device comprises an elongate main body extending between a first, leading end and a second, trailing end, the first, leading end terminating into a tapered nose having a sharp cutting edge, and a series of cutting fins arranged along a helical spiral down the length of the elongate main body. The cutting fins roughen the bone tissue during insertion, thereby initiating a healing response that promotes fusion.

In another embodiment, an implantable device for cervical facet fusion is provided. The device comprises an elongate main body extending between a first, leading end and a second, trailing end, the first, leading end terminating into a tapered nose having a sharp cutting edge, and a plurality of openings along the length of the elongate main body. The openings facilitate bony ingrowth after implantation.

In still another embodiment, an implantable device for cervical facet fusion is provided. The device comprises an elongate main body extending between a first, leading end and a second, trailing end, the first, leading end terminating into a tapered nose having a sharp cutting edge, and a series of cutting fins arranged along a helical spiral down the length of the elongate main body. A plurality of grating holes are also provided along the elongate main body. The cutting fins and grating holes roughen the bone tissue during insertion, thereby initiating a healing response that promotes fusion.

In yet another embodiment, a method of treating degeneration of a facet joint is provided. The method comprises providing an implantable device comprising an elongate main body extending between a first, leading end and a second, trailing end, the first, leading end terminating into a tapered nose having a sharp cutting edge, and a plurality of cutting fins arranged along a helical spiral down the length of the elongate main body; drilling a pilot hole into a targeted site of the facet joint to be treated; inserting the implantable device into the pilot hole; and delivering the implantable device into the targeted site. The facet joint may be a cervical facet joint.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

It is to be understood that both the foregoing general description and the following detailed description are exemplary and explanatory only and are not restrictive of the disclosure. Additional features of the disclosure will be set forth in part in the description which follows or may be learned by practice of the disclosure.

DETAILED DESCRIPTION OF THE EMBODIMENTS

The present disclosure provides implantable devices for the treatment of degenerative facet joint disease, and more specifically to implantable devices for the immobilization or fusion of degenerated facet joints, particularly of the cervical spine. Also provided are methods of implanting and using these devices.

Figure 1A:
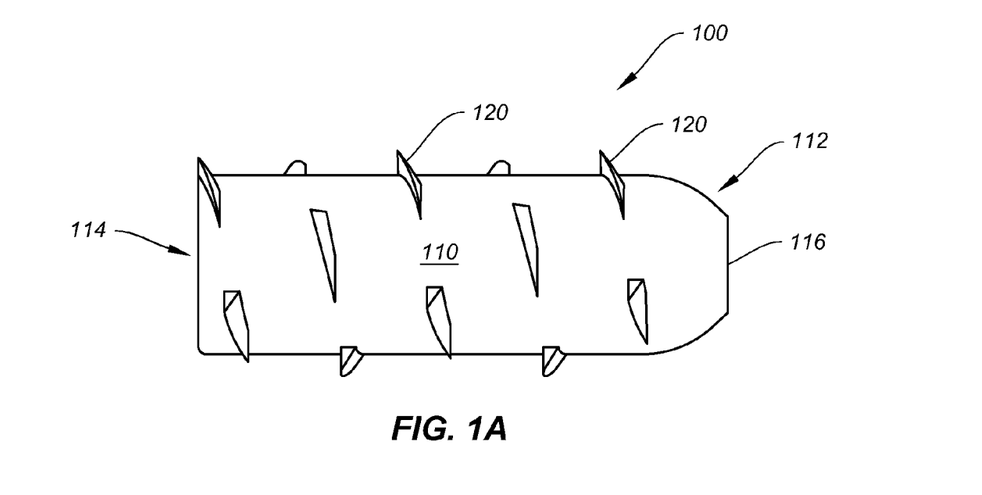
FIG. 1A is a planar side view of an exemplary embodiment of an implantable device of the present disclosure.

Turning now to the drawings, FIG. 1A shows an exemplary embodiment of an implantable device 100 of the present disclosure. Implantable device 100 may comprise an elongate main body 110 terminating at a first, leading end 112 and at a second, trailing end 114 at an opposite end. The first, leading end 112 may taper into a rounded nose 116. However, the nose 116 does not need to be limited to such and could be bullet shaped, conical, or any other shape as desired for ease of insertion.

Figure 1B:
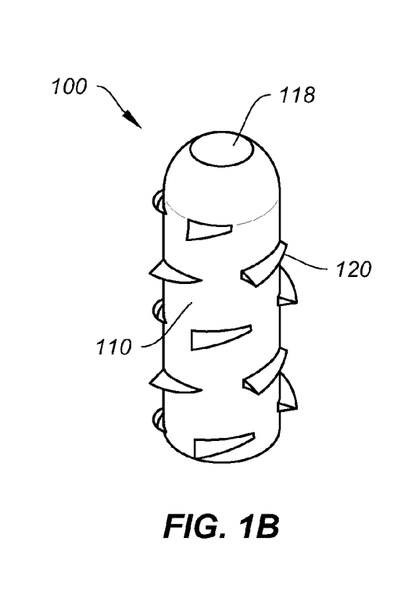
FIG. 1B is a perspective view of the implantable device of FIG. 1A.
Figure 1C:
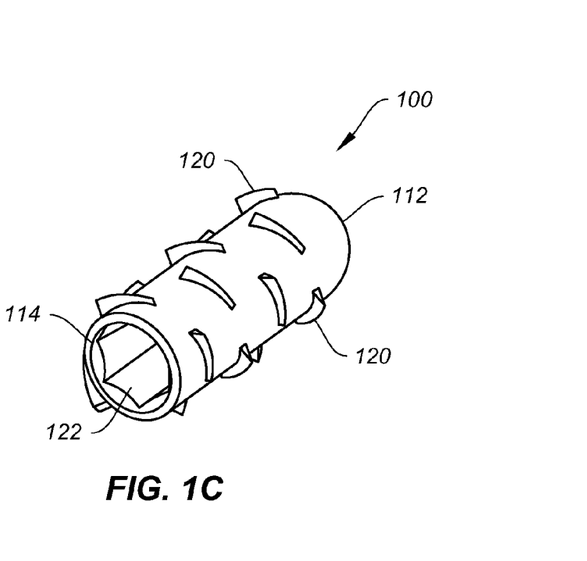
FIG. 1C is another perspective view of the implantable device of FIG. 1A.

The main body 110 may be cannulated, and include a central channel 118 as shown in FIG. 1B. The central channel 118 allows the device 100 to be used with a guidewire during insertion. The device 100 may be inserted through a pre-drilled pilot hole on a diseased facet using a guidewire, for example. A tool-engaging opening 122 at the second, trailing end 114, as shown in FIG. 1C, can be provided to allow the device 100 to quickly attach and detach from a driver tool for insertion into the pre-drilled hole and into the facet. The opening 122 could be, for example, a hex opening as shown, although other configurations are contemplated. For instance, the opening 122 could be threaded to allow a threaded connection with the insertion tool. Other types of connections known to those skilled in the art may be interchangeable with the one shown and described herein.

As further shown in FIGS. 1A-1C, the implantable device 100 may include a plurality of cutting fins 120 on the elongate main body 110. The cutting fins 120 may be oriented in a helical fashion along the main body 110, such that the fins 120, if extended so as to be continuous (i.e., each fin is connected to an adjacent fin) would form a helical thread that runs along the length of the main body 110. It is contemplated that the cutting fins 120 would help to anchor the device 100 into the facet being treated, and prevent the device 100 from backing out. More importantly, the cutting fins 120 would help to initiate a physiological response akin to fracture healing at the site by cutting into, scraping, and generally causing bone bleeding as the device 120 is seated into the facet. In this regard, the cutting fins 120 would also help serve as a mechanical scaffold for new bone growth around and in between the fins 120. Although the fins 120 are shown as wedge-shaped, it is understood that the fins 120 may comprise other shapes, such as V, W or wave-shaped. For instance, the fins 120 may comprise bands of ridges or teeth.

Figure 2A:
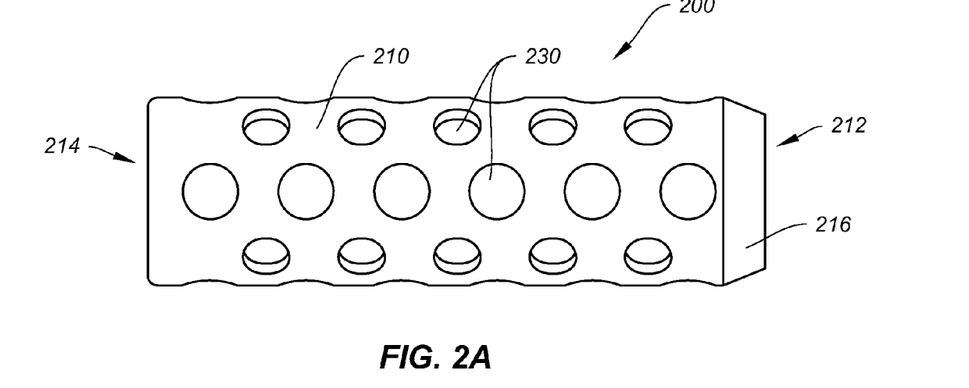
FIG. 2A is a planar side view of another exemplary embodiment of an implantable device of the present disclosure.
Figure 2B:
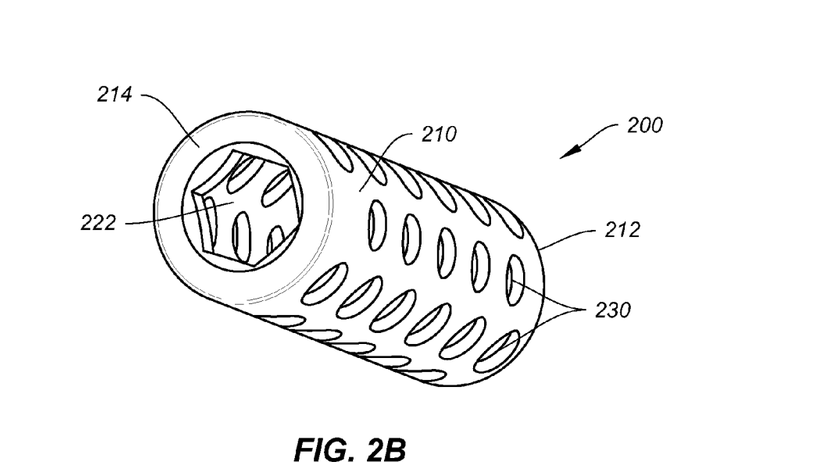
FIG. 2B is a perspective view of the implantable device of FIG. 2A.

FIGS. 2A and 2B illustrate another exemplary embodiment of an implantable device 200 of the present disclosure. Like implantable device 100, this device 200 may comprise an elongate main body 210 that terminates at a first, leading end 212 and at a second, trailing end 214 at the opposite end. The first, leading end 212 may include a tapered nose 216. The tapered nose 216 may have a very sharp terminal edge that facilitates cutting into bone tissue during insertion. This edge could be smooth, or roughened or jagged.

Similar to the previous implantable device 100, the main body 210 may be cannulated for use with a guidewire. Implantable device 200 may be inserted in the same manner as described for implantable device 100, and further as will be described below. Accordingly, the second, trailing end 214 of the implantable device 200 may include a tool-engaging opening 222, as shown in FIG. 2B. Implantable device 200 may further include a plurality of openings 230 along the length of the main body 210. These openings 230 may allow for bony ingrowth through the device 200.

Figure 3A:
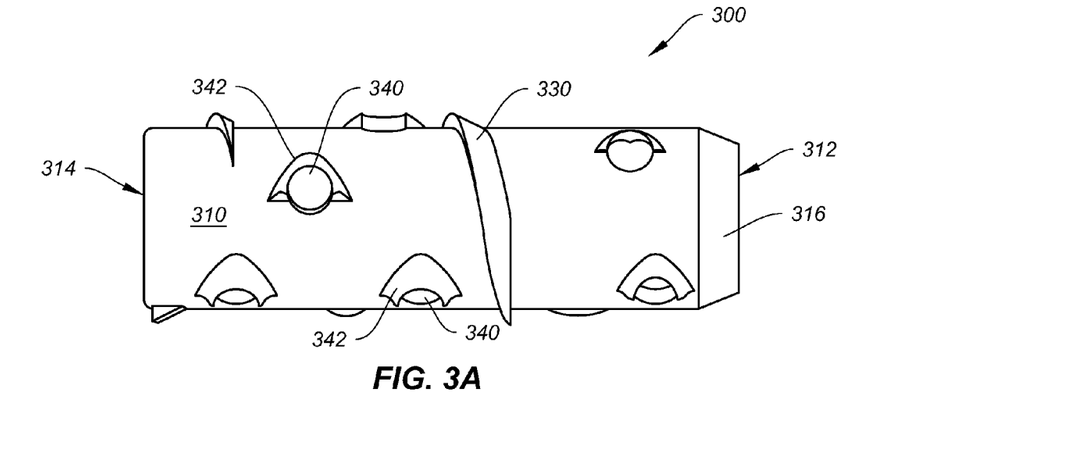
FIG. 3A is a planar side view of yet another exemplary embodiment of an implantable device of the present disclosure.
Figures 3B, 3C:
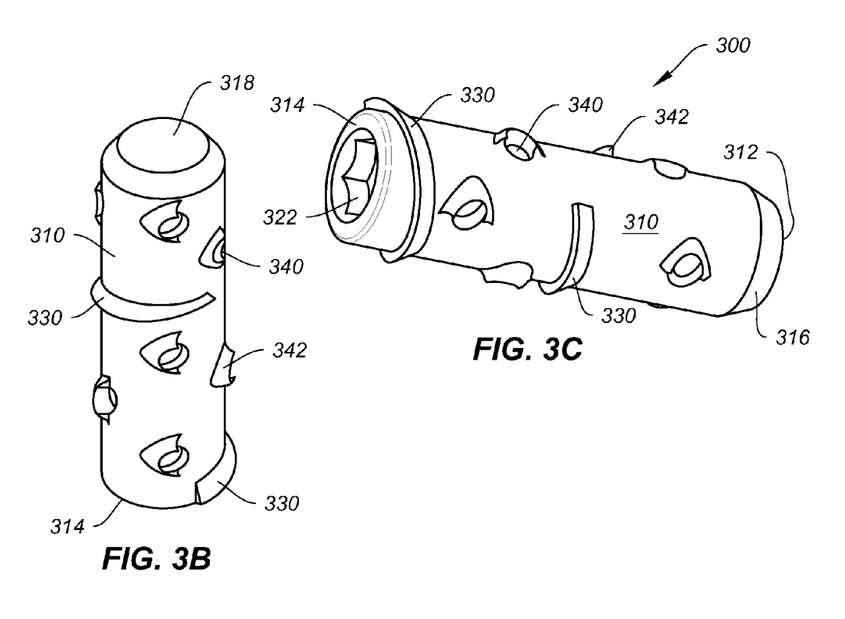
FIG. 3B is a perspective view of the implantable device of FIG. 3A.
FIG. 3C is another perspective view of the implantable device of FIG. 3A.

FIGS. 3A-3C illustrate yet another exemplary embodiment of an implantable device 300 of the present disclosure. Implantable device 300 combines some of the features present in each of the implantable devices 100, 200 previously described. Implantable device 300 may comprise an elongate main body 310 having a first, leading end 312 and a second, trailing end 314 at an opposite end. The first, leading end 312 may have a tapered nose 316. The tapered nose 316 may be configured to have a very sharp terminal edge to facilitate cutting into bone tissue during insertion. The terminal edge could be smooth, as shown, or it could also encompass a jagged, roughened edge if so desired.

The main body 310 may be cannulated and include central channel 318 for use with a guidewire. As will be described in more detail below, the second, trailing end 314 of the implantable device 300 may be configured with a tool-engaging opening 322, as shown in FIG. 3C. This opening 322 allows the device 300 to be attached to an insertion tool for driving the device 300 into the bone to be treated.

Along the length of the main body 310 are cutting fins 330 that may be oriented in a helical-spiral fashion. The fins 330 may be wedge-shaped, as shown. Alternatively, the cutting fins 330 may comprise other shapes, such as S, V, W or wave-shapes. For instance, the cutting fins 330 may comprise bands of ridges or teeth.

Also on the main body 310 are grating holes 340. These grating holes 340 include a raised cover 342 having a sharp, cutting edge as shown in FIGS. 3A and 3B that resides over a portion of the grating hole 340. In use, as the implantable device 300 is inserted, the cutting fins 330 and grating holes 340 help to cut into and scrape the pre-drilled hole in the facet bone where the device 300 is being placed. Excess bone tissue may be directed inside the main body 310 through the grating holes 340, while the cutting fins 330 help to anchor the device 300 in the bone and prevent the device 300 from backing out. In some cases, the grating holes 340 may allow for some bony ingrowth into the device 300.

Figure 4:
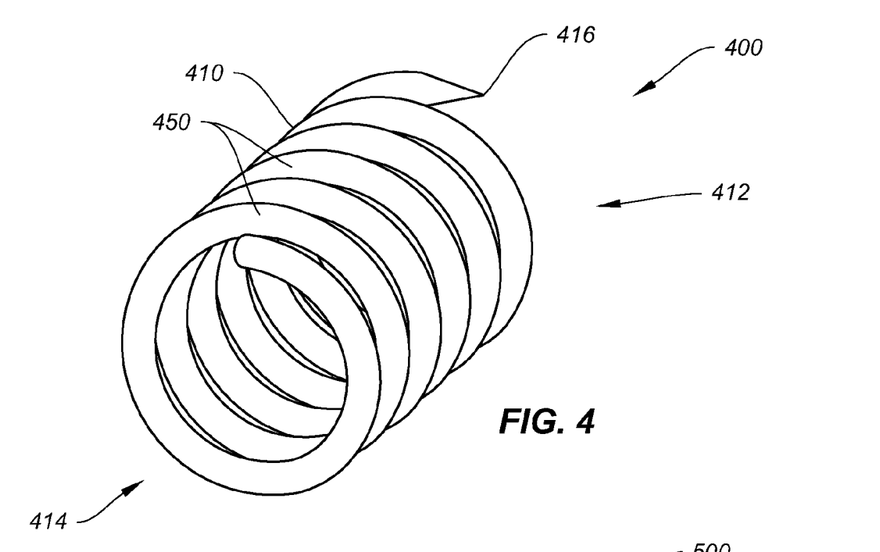
FIG. 4 is a perspective view of still another exemplary embodiment of an implantable device of the present disclosure.

FIG. 4 illustrates still yet another exemplary embodiment of an implantable device 400 of the present disclosure. Implantable device 400 may comprise an elongate main body 410 having a first, leading end 412 and a second, trailing end 414 at an opposite end. The first, leading end 412 may have a tapered, sharp tip 416 for piercing through bone and surrounding tissue. Additional structural features could be provided on the tip 416 to facilitate its cutting into bone tissue during insertion, such as for example, barbs, threads, or raised cutaway portions to create a jagged cutting edge. The tip 416 may extend into a series of helically wound coils 450 all the way to the second, trailing end 414. These coils 450 may be packed, or wound closely together, or they may be configured with a gap in between. The coiled body 410 serves as a fusion cage, and can allow bone growth to occur throughout, thereby further enhancing anchorage of the implantable device 400 to the patient's anatomy.

Figure 5:
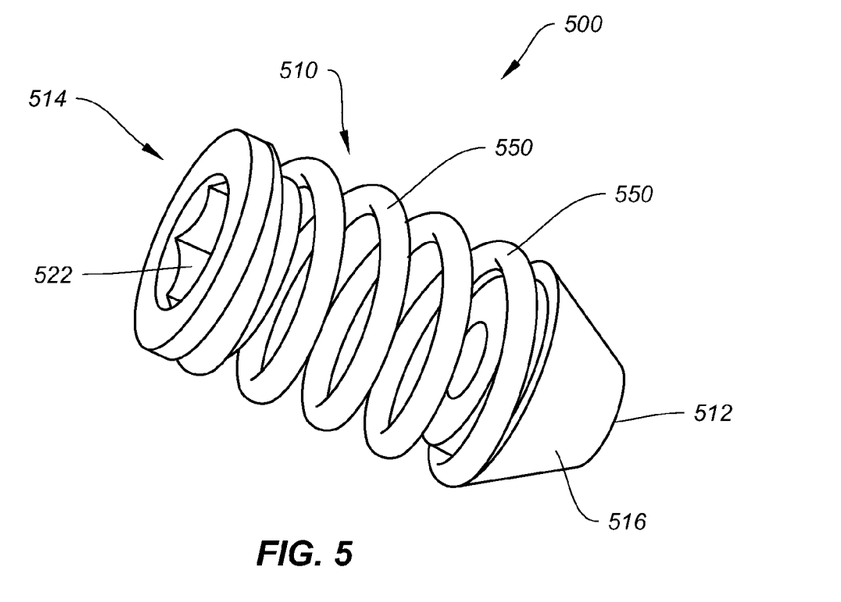
FIG. 5 is a perspective view of even still another exemplary embodiment of an implantable device of the present disclosure.

FIG. 5 illustrates even still another exemplary embodiment of an implantable device 500 of the present disclosure. Implantable device 500 may comprise an elongate main body 510 having a first, leading end 512 and a second, trailing end 514 at an opposite end. Like in previous embodiments, the first, leading end 512 may include a tapered nose 516 to ease insertion into the bone. The tapered nose 516 may have a very sharp terminal edge, or include surface features such as barbs, threads, or cutaway portions to create a jagged cutting edge to facilitate cutting into bone tissue during insertion. The second, trailing end 514 may further include a tool-engaging opening 522 to allow the device 500 to be attached to an insertion tool for driving the device 500 into the bone to be treated.

The main body 510 may comprise a series of helically wound coils 550 extending from the tapered nose 516 to the second, trailing end 514. Similar to implantable device 400, these coils 550 may be packed, or wound closely together, or they may be configured with a gap in between. Similarly, the coiled body 510 may serve as a cage, and allow bone growth to occur throughout, thereby further enhancing anchorage of the implantable device 500 to the patient's anatomy.

While implantable devices 100, 200, 300 can have a general appearance of, and function similarly to, a bone screw, implantable devices 400, 500 can have a general appearance of, and function more similarly to, fusion cages. Thus, it can be appreciated that the implantable devices of the present disclosure may share numerous structural designs to other fusion-promoting devices currently known to achieve the desired result.

The implantable devices 100, 200, 300, 400, 500 of the present disclosure may be formed of any suitable medical grade metal. Suitable metals may include, but are not limited to, stainless steel, titanium, titanium alloys, and cobalt chrome, as examples. Porous metals may also be appropriate. Of course, the devices 100, 200, 300 may also be formed from a variety of other suitable biocompatible materials, either alone or in combination with one another. The devices may also be ABS injection molded plastic, polyetheretherketone (PEEK), polyethylene (PE), or ultra high molecular weight polyethylene (UHMWPE). If desired, the devices may be bioabsorbable or bioresorbable. In other embodiments, the implant may be formed partially or wholly from a radiolucent material. For example, the implant may be formed from a material blended with a radiopaque material, such as barium sulfate. In addition, radiopaque markers may be employed with the implant for imaging possibilities. Where a semi-rigid implantable device is desirable, it is possible to combine rigid materials with other semi-flexible materials such as silicone or another rubber-like material to form a semi-rigid, semi-flexible device that is still capable of withstanding normal compression loads.

Other examples of suitable synthetic polymers include, but are not limited to, polyvinyl alcohol (PVA) and alkylated or acylated derivatives thereof, polyurethane (PU), polypropylene (PP), nylon, polycaprolactone (PCL), and copolymers and combinations thereof. Examples of suitable synthetic non-biodegradable polymers, include, but are not limited to, various polyacrylates, ethylene-vinyl acetates (and other acyl-substituted cellulose acetates), polystyrenes, polyvinyl oxides, polyvinyl fluorides, poly(vinyl imidazoles), chlorosulphonated polyolefins, polyethylene oxides, polytetrafluoroethylenes and nylons. Another polymeric material, which is particularly suitable for use in production of mouldable compositions, is a hydrolysed polymer or copolymer of a vinyl ester, particularly a hydrolysed polymer or copolymer of vinyl acetate.

In addition, the implantable devices 100, 200, 300, 400, 500 of the present disclosure can be enhanced with biologically active features to promote fusion and new bone growth. In one embodiment, the biologically active feature may be native to the material forming the device. For instance, the device may be formed entirely of or coated with bioactive glass ("BAG"). In another embodiment, the surface of the implantable devices 100, 200, 300, 400, 500 may include biologically active agents. The biologically active agent may be contained in a coating on the device 100, 200, 300, 400, 500. These agents may include osteoconductive, osteoinductive, or osteogenic factors to further facilitate bonding between the devices 100, 200, 300, 400, 500 and the surrounding bone tissue. The biologically active agent may be, for example, bone morphogenic protein (BMP) for modulating cartilage or bone growth, platelet rich plasma (PRP), bone marrow aspirate (BMA), demineralized bone matrix (DBM), stem cells, or allograft material, for example. Furthermore, a bioactive surface may be created on the devices by treating the implantable devices with, for example, acid etching, grit blasting, plasma spraying, bioactive glass coating, photo-chemical etching, or other suitable surface treatments for creating a roughened surface. Additionally, the implantable devices 100, 200, 300, 400, 500 may include therapeutic agents such as antibiotics, steroids, anti-thrombotic agents, anti-inflammatory drugs, and/or analgesic agents.

Alternatively, or in addition, these agents may be embedded within the devices. For example, the device may be porous, and the biologically active agent may be contained in the pores of the device. In still another embodiment, the biologically active feature may be a separate component usable in combination with the device. For instance, a bone graft insert may be employed inside the devices 100, 200, 300, 400, 500 of the present disclosure.

Figure 6A:
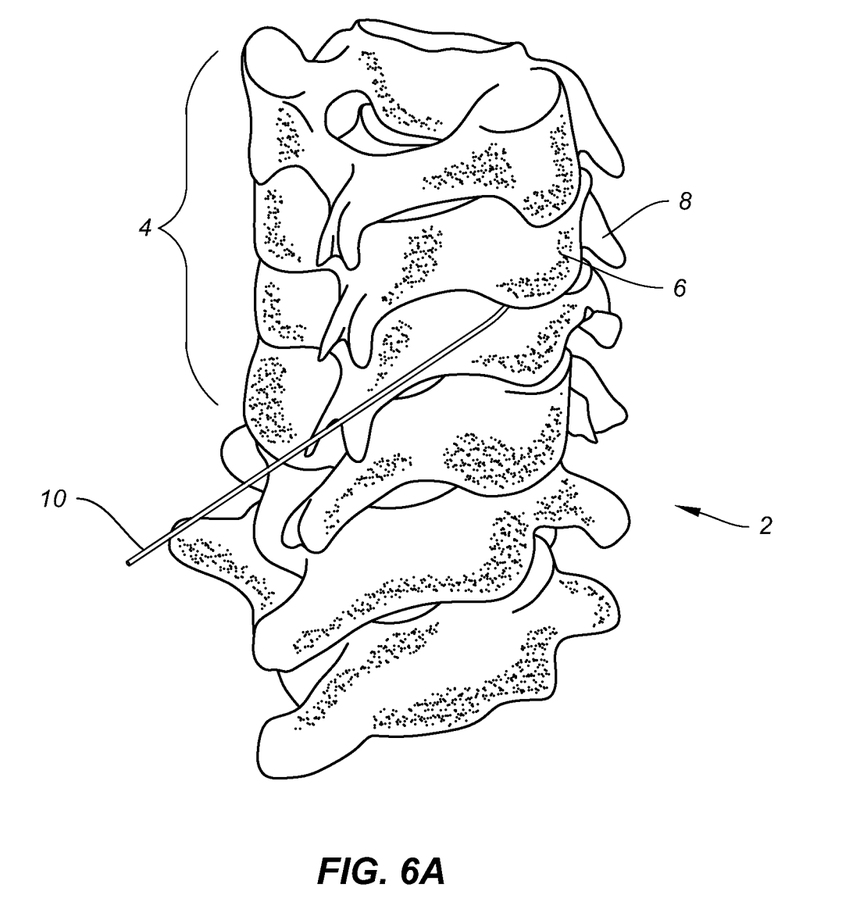
FIGS. 6A-6I illustrate an exemplary method of inserting the implantable devices into a facet joint of the cervical spine.
Figure 6B:
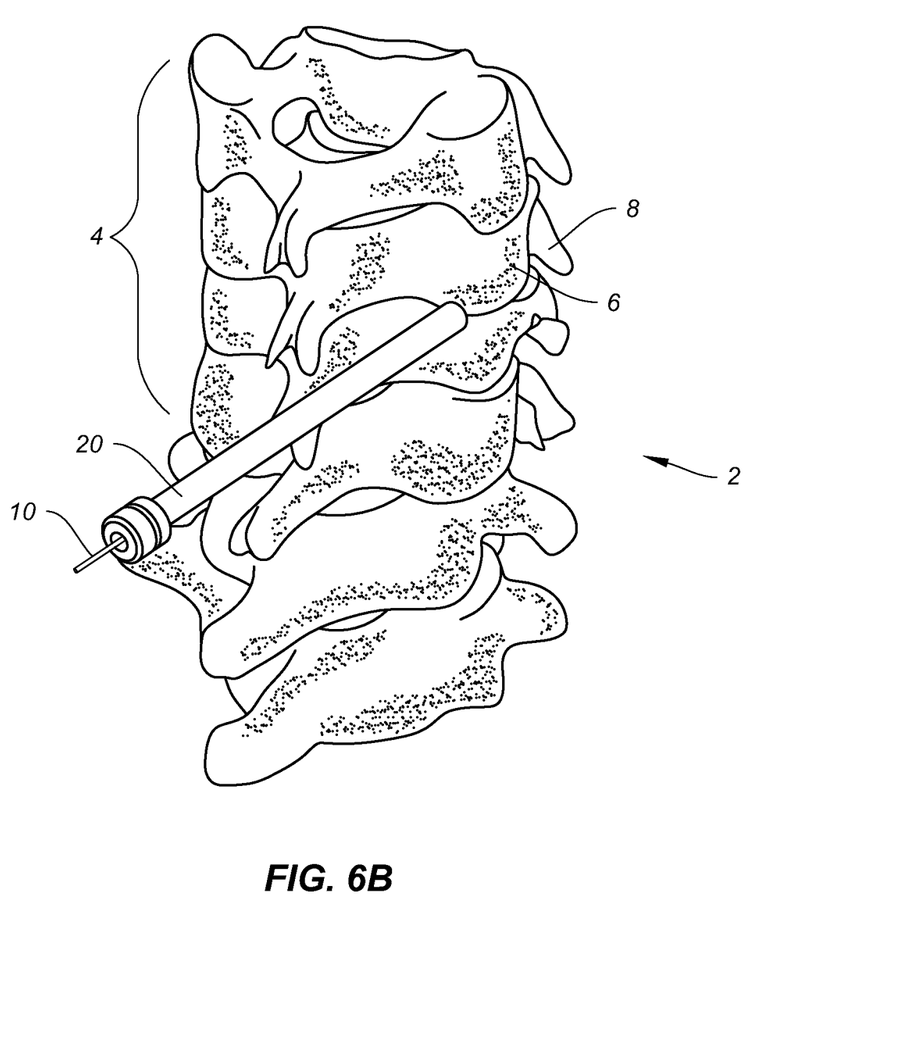
Figure 6C:
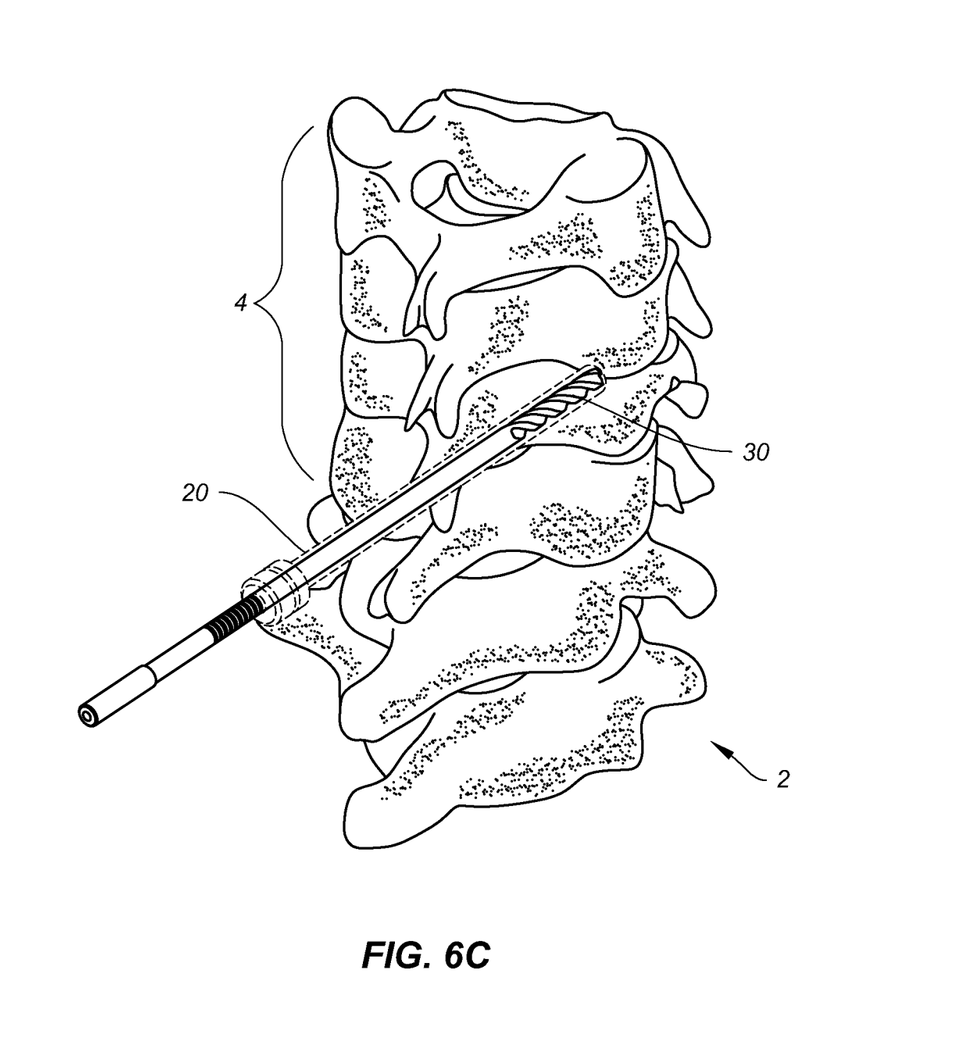

The implantable devices 100, 200, 300, 400, 500 of the present disclosure may be used to treat degenerative facet disease or facet arthritis. FIGS. 6A-6G illustrate an exemplary method of using implantable devices 100, 200 to treat a diseased facet joint that needs immobilizing due to degradation. The facet joint 8 may be part of a vertebra 6 in the cervical portion 4 of a patient's spine 2. As shown in FIG. 6A, a guidewire 10 may be inserted into the targeted facet 8 to be treated. Once the guidewire 10 has been properly placed, a dilator tube or cannula 20 may be placed over the guidewire 10, as shown in FIG. 6B. Then, a drill bit 30 may be placed through the cannula 20, as shown in a cutaway view of FIG. 6C. Next, a pilot hole is drilled into the facet joint 8 to receive the implantable device 100, 200. The pilot hole may have a slightly smaller diameter than the outer diameter of the implantable device 100. For example, the pilot hole could be approximately 2.7 mm in diameter for a 3.0 mm device.

Figures 6D, 6E:
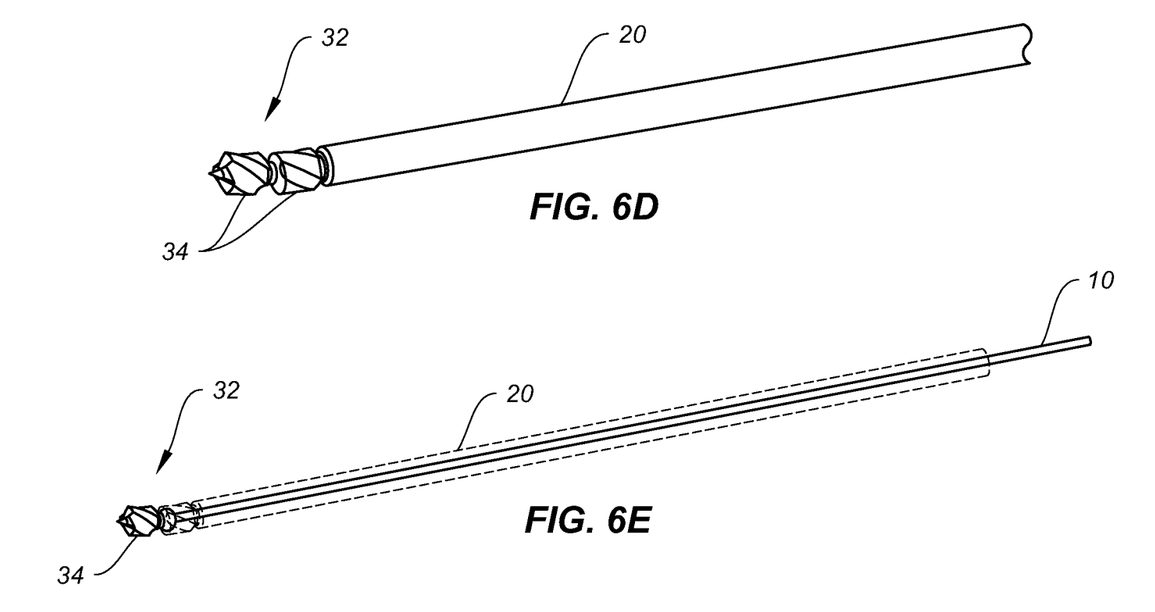

Due to the very tight space surrounding the cervical spine 4, the relative curvatures of the patient's natural anatomy are even more pronounced in this cervical region 4 of the spine 2. Thus, it is desirable to provide a drill bit 30 that may be able to bend or curve along with the contours of the facet or facet joint 8. FIGS. 6D and 6E illustrate one exemplary embodiment of a multi-linked articulating drill bit 32 comprising one or more drill bits 34 that can be independently controlled so that the clinician or user may be able to achieve a more angular or curved approach. The entire drilling process may be done over the guidewire 10. Proper drilling techniques are critical to the success of the method, since the drilling acts as burring or debridement, stimulating the patient's natural healing response. In addition, proper drilling into the narrow structure of the weakened facet 8 will prevent over-drilling or over-angulation that could cause further damage to the weakened structure and cause breakage of the existing bone.

Figure 6F:
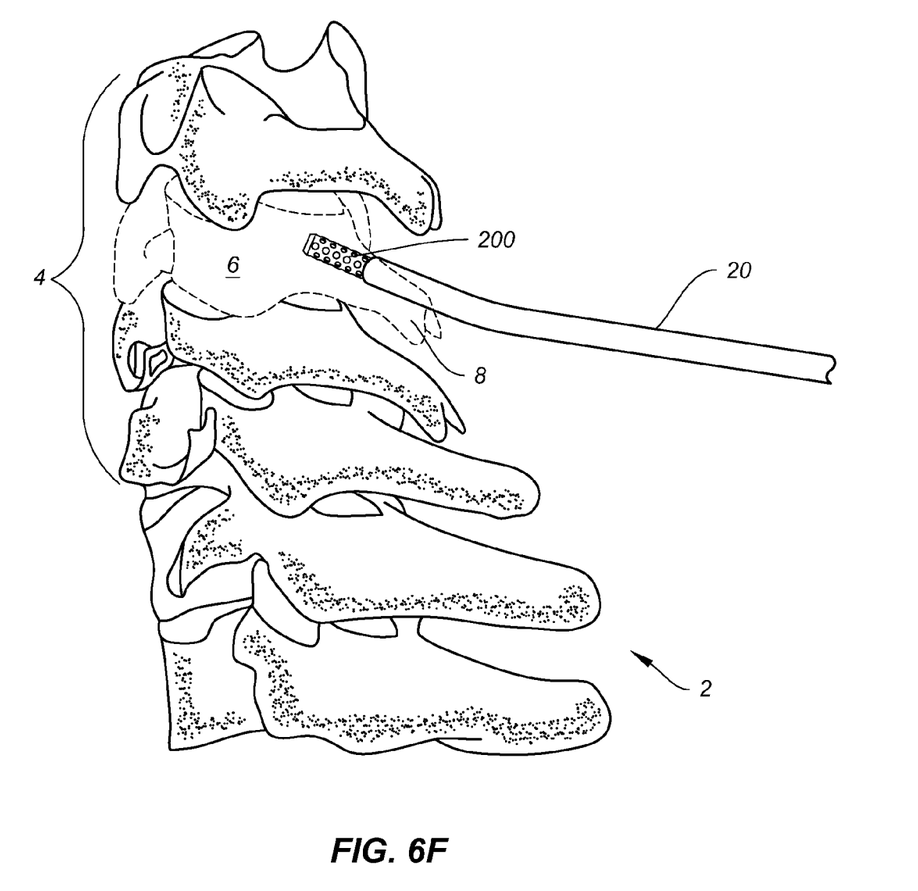

Once the pilot hole and insertion path has been achieved, the implantable device may be inserted into the facet joint 8. As shown in FIG. 6F in which implantable device 200 is being delivered, the device 200 may be delivered along the same path as the drill bit 32 previously made. It would be preferable for the cannula 20 to allow some bending as well, as illustrated in FIG. 6F, to facilitate ease of insertion. Having the ability to bend slightly and conform to the contours of the patient's anatomy will reduce the overall force needed to be exerted, and prevent breakage or damage due to excessive force. Thus, as shown, a flexible cannula 20 could be preferably used in this method.

Figure 6G:
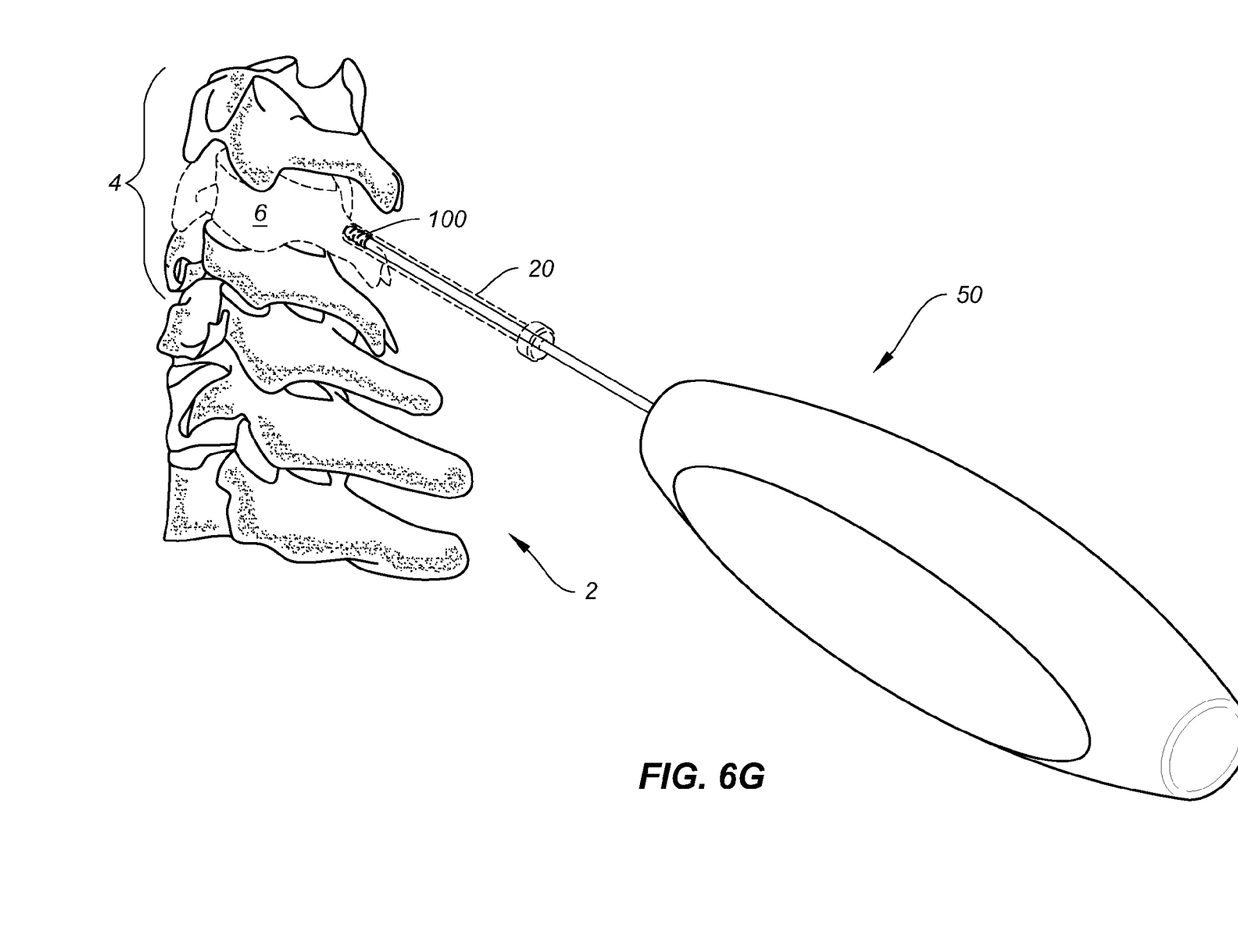

As FIG. 6G illustrates, implantable device 100 may be attached at its tool-engaging end to a driver such as an insertion tool 50 as is commonly used in the art. The implantable device 100 may then be inserted through cannula 20 into the pilot hole with slight twisting action to seat the device 100 inside the hole. The pilot hole itself may be in the range of about 6-9 mm in length to accommodate an implantable device of about the same length. In some cases, the implantable device 100 may be press fitted into place.

As the implantable device 100 is inserted, it is contemplated that the cutting fins 120 would help to initiate a physiological response akin to fracture healing at the site by roughening up the bone tissue of the pilot hole. The cutting and scraping of bone tissue, along with bone bleeding, triggers a healing response or fusion of the joint. The implantable device 100 further serves as a mechanical scaffold for new bone growth around and in between the fins 120, which also help avoid back out. In the case of implantable device 300, the grating holes 340 would allow for some of the scraped bone tissue to be scooped into the main body 310, thereby also allowing bony ingrowth through the device 300.

Figure 6H:
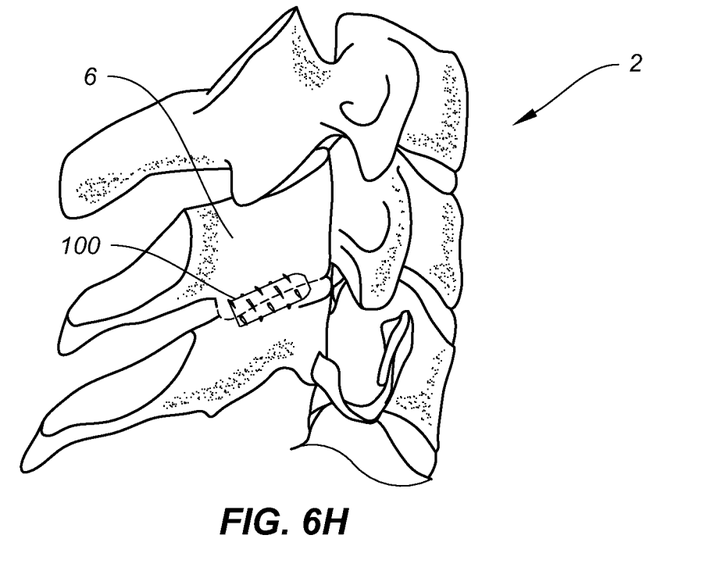

FIG. 6H illustrates the implantable device 100 in situ, properly situated within the facet joint being treated. Once the implantable device 100 is in place, the same steps may be repeated on the other side of the spine 2. It is contemplated that the entire process can be performed using fluoroscopy for visualization.

While the invention is described in the context of osteoarthritis of the spine, and particularly the cervical spine, it is not limited to such condition. Other conditions that can be treated in accordance with the invention include but are not limited to osteoarthritis of joints other than the spine. For example, the implantable devices may be used to treat other joints, such as the shoulder, hip, and knee. In particular, the implantable devices of the present disclosure may have particular applicability in small bone joints such as the ankle, foot, hand, and fingers. Moreover, in some embodiments, the implantable devices may be coupled to other forms of joint pain treatment. For instance, implantation of the facet fusion devices may be employed in conjunction with other procedures. In such cases, the implantable device itself becomes a component in a multi-step treatment process to address the overall pain management and treatment of the joint.

In another embodiment, the implantable devices 100, 200, 300, 400, 500 may be inserted along a perpendicular plane into the facet joint. As described above and as shown in FIGS. 6A-6H, the implantable devices are inserted along the facet joint line, or along the joint plane. For instance, one method of implanting the device would approach from the posterior and medial, and angle anterolateral along the plane of the joint.

Figure 6I:
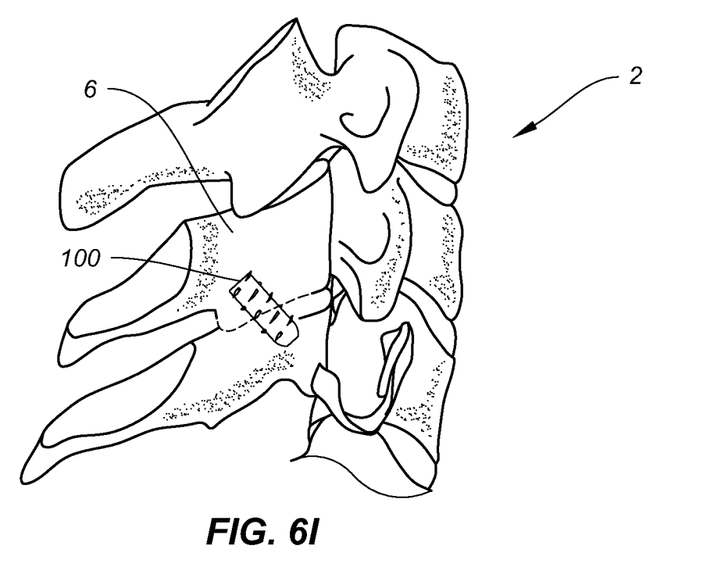

However, it is contemplated that the implantable devices of the present disclosure could also be inserted so as to cross the facet joint line, as shown in FIG. 6I. In such an arrangement, the implantable device would reside in a plane perpendicular to the joint plane. In this embodiment the approach would still be from the posterior, but would come from a superior to inferior angle crossing the joint, rather than inferior to superior along the joint plane. That is, the implantable device could be inserted from the posterior and medial, and angle inferior and lateral across the joint.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. An implantable device for cervical facet fusion, comprising:
   an elongate main body having a central channel and extending between a first, leading end and a second, trailing end, the first, leading end terminating into a tapered nose, a plurality of cutting fins extending in a helical direction along the length of the elongate main body, the cutting fins being configured to scrape away bone tissue as the device is inserted into bone, the elongate body further including a plurality of grating holes extending along the length of the elongate main body, each of the grating holes being configured as a through-hole in communication with the central channel and having a corresponding curved, raised cover extending thereover, each cover having a sharp cutting edge for scraping tissue as the device is inserted into bone and the grating holes being configured to receive the scraped bone tissue;
   wherein the shape of the cutting fins is different than the shape of the covers, and at least some of the grating holes and covers are located between the cutting fins.

2. The device of claim 1, further including a tool-engaging opening at the second, trailing end.

3. The device of claim 1, wherein the elongate main body is cannulated.

4. The device of claim 1, further being biologically active.

5. The device of claim 4, wherein the device includes a biologically active coating.

6. The device of claim 4, wherein the device is formed of a biologically active material.

7. The device of claim 4, wherein the device includes a biologically active material.

8. An implantable device for cervical facet fusion, comprising:
- an elongate main body having a central channel and extending between a first, leading end and a second, trailing end, the first, leading end terminating into a tapered nose, and a plurality of cutting fins and grating holes along the length of the elongate main body;
- wherein the cutting fins are configured with sharp edges and the grating holes are configured as through-holes in communication with the central channel, each of the grating holes having a curved, raised cover extending thereover, each cover having a sharp cutting edge so that bone tissue is scraped away as the device is inserted into bone, the grating holes being configured to receive the scraped bone tissue;
- further wherein the shape of the cutting fins is different than the shape of the covers, and at least some of the grating holes and covers are located between the cutting fins.

9. A method of treating degeneration of a facet joint, comprising:
- providing an implantable device comprising an elongate main body having a central channel and extending between a first, leading end and a second, trailing, the first, leading end terminating into a tapered nose, and a plurality of cutting fins and grating holes arranged along the length of the elongate main body, the cutting fins being configured with sharp edges and the grating holes being configured as through-holes in communication with the central channel, each of the grating holes having a curved, raised cover extending thereover, each cover having a sharp cutting edge to scrape away bone tissue as the device is inserted into bone, the grating holes further being configured to receive the scraped bone tissue, wherein the shape of the cutting fins is different than the shape of the covers, and at least some of the grating holes and covers are located between the cutting fins;
- drilling a pilot hole into a targeted site of the facet joint to be treated;
- inserting the implantable device into the pilot hole; and
- delivering the implantable device into the targeted site.

10. The method of claim 9, wherein the facet joint is a cervical facet joint.

11. The method of claim 9, wherein the step of drilling causes debridement.

12. The method of claim 9, wherein the pilot hole has a diameter smaller than an outer diameter of the implantable device.

13. The method of claim 9, wherein the pilot hole is non-linear.

14. The method of claim 13, further including the step of using an articular drill bit to drill the pilot hole.

15. The method of claim 9, further including the step of inserting a guidewire to the targeted site of the facet joint to be treated.

16. The method of claim 9, further including the step of identifying a second targeted site of a facet joint to be treated, the second targeted site located on an opposite side of the spine.

17. The method of claim 16, further including repeating the steps of drilling, inserting and delivering to the second, targeted site.

18. The method of claim 9, wherein the implantable device is placed along a plane of the facet joint.

19. The method of claim 9, wherein the implantable device is placed across the facet joint.

* * * * *